(12) United States Patent
Crowley (10) Patent No.: US 11,865,304 B1
(45) Date of Patent: Jan. 9, 2024

(54) SHIELDED SYSTEM FOR AUTOMATED ADMINISTRATION OF NUCLEAR MEDICATION

(71) Applicant: James R Crowley, Roanoke, VA (US)

(72) Inventor: James R Crowley, Roanoke, VA (US)

(73) Assignee: Carilion Clinic, Roanoke, VA (US)

( * ) Notice: Subject to any disclaimer, the term of this patent is extended or adjusted under 35 U.S.C. 154(b) by 470 days.

(21) Appl. No.: 17/175,809

(22) Filed: Feb. 15, 2021

Related U.S. Application Data (60) Provisional application No. 62/976,288, filed on Feb. 13, 2020, provisional application No. 62/976,285, filed on Feb. 13, 2020.

(51) Int. Cl.
*A61M 5/20* (2006.01)
*A61M 5/178* (2006.01)
*A61M 5/168* (2006.01)

(52) U.S. Cl.
CPC ...... *A61M 5/1785* (2013.01); *A61M 5/16886* (2013.01); *A61M 5/20* (2013.01); *A61M 2205/3331* (2013.01)

(58) Field of Classification Search
CPC .. A61M 5/1785; A61M 5/16886; A61M 5/20; A61M 2205/3331
USPC ......... 250/505.1, 506.1, 507.1, 515.1, 516.1, 250/517.1, 518.1, 519.1
See application file for complete search history.

(56) References Cited

U.S. PATENT DOCUMENTS

2008/0242915 A1* 10/2008 Jackson ................... G21H 5/02
600/4
2021/0268187 A1* 9/2021 Gertsenchtein ......... G21F 5/018

* cited by examiner

*Primary Examiner* — Nicole M Ippolito
(74) *Attorney, Agent, or Firm* — Rhodes IP PLC; Christopher Rhodes (57) ABSTRACT

Certain configurations of devices and systems that can administer a nuclear medication in an automated manner are described. In some instances, the system can receive a nuclear medication in a shielded transport container and administer the nuclear medication to a patient through an intravenous line in an automated manner to minimize radiation exposure by staff. Methods of using the devices and systems are also described.

20 Claims, 7 Drawing Sheets

SHIELDED SYSTEM FOR AUTOMATED ADMINISTRATION OF NUCLEAR MEDICATION

PRIORITY APPLICATION

This application claims priority to, and the benefit of, each of U.S. Provisional Application No. 62/976,288 filed on Feb. 13, 2020 and U.S. Provisional Application No. 62/976,285 filed on Feb. 13, 2020. The entire disclosure of each of these applications is hereby incorporated herein by reference.

BACKGROUND

Administration of radioactive therapeutic materials often leads to unwanted exposure of staff to the radioactivity. Staff are often required to wear personal protective equipment (PPE) to reduce their exposure to the radioactive therapeutic materials. This PPE can be bulky and heavy and is prone to human error.

SUMMARY

Certain aspects, configurations and embodiments are described of systems that can be used to deliver a nuclear medication to a patient in an automated manner. The systems can be designed to reduce or minimize exposure of staff members to the nuclear medication during administration.

In an aspect, a system for delivering a nuclear medication to a patient comprises a cradle, a lid, an actuator assembly and a processor. In some configurations, the cradle can be configured to receive a shielded transport container, wherein the shielded transport container is constructed and arranged to receive a syringe with the nuclear medication. In certain embodiments, the lid is configured to permit placement of the shielded transport container into the cradle in an open position and block access to the cradle in a closed position, wherein the lid is configured to shield an external user from radiation emitted from the nuclear medication in the syringe when the lid is in the closed position. In some examples, the actuator assembly can include a first actuator configured to contact and remove access covers of the shielded transport container to expose a needle end of the syringe and to expose a plunger of the syringe. For example, the first actuator can be further configured to position the exposed needle end of the syringe to align the needle end of the syringe with an intravenous injection port fluidically coupled to an intravenous line connected to the patient. In some embodiments, the actuator assembly can also include a second actuator configured to engage and depress the exposed plunger of the positioned syringe to inject the nuclear medication into the intravenous injection port. In some embodiments, the processor can be configured to control the first actuator and the second actuator so that the nuclear medication can be delivered to a patient in an automated manner.

In certain embodiments, the second actuator can be configured to inject the nuclear medication into the intravenous injection port incrementally over an infusion period. In some embodiments, the first actuator is configured as a rotary actuator. In other embodiments, the second actuator is configured as a linear actuator. In some examples, each of the first actuator and the second actuator comprises a motor. In other examples, the system can include a pressure sensor, wherein the pressure sensor is configured to measure pressure in the intravenous line during infusion of the nuclear medication to the patient. In some embodiments, the system can include a lock configured to lock the lid in the closed position when the lid is closed after the shielded transport container is placed in the cradle. In certain embodiments, the processor is configured to automatically actuate the first actuator after closing the lid. In other embodiments, the first actuator is configured to rotate an access cover off of each end of the shielded transport container to expose the needle and the plunger. In some embodiments, the system can include a display configured to permit entry of treatment parameters into the system.

In another aspect, a method of administering a nuclear medication to a patient is described. In certain configurations, the method comprises injecting a nuclear medication from a syringe into an intravenous line of the patient in an automated manner after positioning the syringe into a system that shields an external user from radiation emitted by the nuclear medication, wherein the syringe is positioned within a shielded transport container received by the system, and wherein access covers of the shielded transport container are removed automatically by the system prior to injecting the nuclear medication from the syringe into the intravenous line.

In certain embodiments, the system that can implements the method can include a cradle configured to receive a shielded transport container, wherein the shielded transport container is constructed and arranged to receive the syringe with the nuclear medication. The system can also include a lid configured to permit placement of the shielded transport container into the cradle in an open position and block access to the cradle in a closed position, wherein the lid is configured to shield the external user from radiation emitted from the nuclear medication in the syringe when the lid is in the closed position. The system can also include a first actuator configured to contact and remove access covers of the shielded transport container to expose a needle end of the syringe and to expose a plunger of the syringe, wherein the first actuator is further configured to position the exposed needle end of the syringe to align the needle end of the syringe with an intravenous injection port fluidically coupled to an intravenous fluid line connected to the patient. The system can also include a second actuator configured to engage and depress the exposed plunger of the positioned syringe to inject the nuclear medication into the intravenous injection port. The system can also include a processor configured to control the first actuator and the second actuator. In certain embodiments, the first actuator is configured to rotate an access cover off of each end of the shielded transport container to expose the needle and the plunger. In some embodiments, the processor is configured to automatically actuate the first actuator after closing the lid.

In other embodiments, the method comprises measuring pressure in the intravenous line during infusion of the nuclear medication to the patient. In some examples, the method comprises controlling the second actuator to control the infusion rate of the nuclear medication. In certain embodiments, the method comprises measuring the radioactivity levels of the medication during infusion of the medication. In some examples, the radioactivity levels can be measured using a radiometric sensor. For example, a radiometric sensor can be positioned within the system or can be positioned external to the system.

In another aspect, a radiation shielded transport device comprises a first access cover comprising a radiation shielding material, a second access cover comprising a radiation shielding material, and a body configured to couple to the first access cover at a first end of the body and couple to the second access cover at a second end of the body. In some configurations, the body comprises a radiation shielding material and is configured to receive a barrel of a syringe and retain the syringe barrel in the body.

In certain embodiments, body comprises threads at the first end and at the second end. In other embodiments, the body comprises a spring-loaded button at the first end, and wherein the first access cover comprises a hole configured to receive the spring-loaded button at the first end to retain the first access cover to the first end of the body. In some examples, the first access cover comprises a spring-loaded button, and wherein the body comprises a hole at the first end to receive the spring-loaded button to retain the first access cover to the first end of the body. In certain embodiments, the radiation shielding material of each of the first access cover, the second access cover and the body is independently selected from the group consisting of lead, antimony, bismuth, tungsten and tin. In some examples, the first end of the body is configured to receive and retain the first access cover through a friction fit. In other examples, the second end of the body is configured to receive and retain the second access cover through a friction fit. In additional embodiments, the body comprises a cylindrically shaped outer cross-section. In further examples, each of the first access cover and the second access cover comprises a cylindrically shaped outer cross-section. In some embodiments, the body comprises a cylindrically shaped inner cross-section.

In an additional aspect, a system for delivering a nuclear medication in a syringe to a patient in need of treatment comprises a receiving means and an actuating means. In some embodiments, the receiving means is configured to receive a shielded transport container comprising the syringe with the nuclear medication. For example, the receiving means can be configured to permit placement of the syringe into the system in a first position and prohibit access to the syringe in a second position. The receiving means can also shield an external user from radiation emitted by the nuclear medication in the syringe when the receiving means is in the second position. In some embodiments, the actuating means is configured to fluidically couple the syringe to an intravenous fluid line. The actuating means can also remove an access cover from the shielded transport container to expose a needle end of the syringe. The actuating means can also be configured to position the syringe to align a needle end of the syringe with an intravenous injection port fluidically coupled to the intravenous fluid line. The actuating means can also be configured to engage a plunger of the positioned syringe to inject the nuclear medication into the intravenous injection port.

In another aspect, a system for delivering a nuclear medication to a patient can be configured to standardize flow rate and remove human hands from selecting a flow rate of the nuclear medication.

In an additional aspect, a system for delivering a nuclear medication to a patient can be configured to standardize flow rate under medical direction to reduce infiltration and dose delivery error of the nuclear medication.

In another aspect, a system for delivering a nuclear medication to a patient can be configured to remove human hands from dose delivery of the nuclear medication to reduce radiation dose to staff.

In an additional aspect, a system for delivering a nuclear medication to a patient can be configured to add distance between the staff and the patient to reduce and lower radiation exposure to the staff.

In another aspect, a system for delivering a nuclear medication to a patient can be configured to remove heavy syringe shields from hands of staff to reduce error and expense of syringe shield devices.

In an additional aspect, a system for delivering a nuclear medication to a patient can be configured to utilize unit dose in an automated manner to improve regulatory compliance and reduce/eliminate punctures on bulk vials.

Additional aspects, configurations, embodiments and examples are described in more detail below.

BRIEF DESCRIPTION OF THE SEVERAL VIEWS OF THE DRAWINGS

Certain illustrative embodiments are described below with reference to the figures in which.

The illustrations in the figures do not necessarily show the components to scale or all components that can be present in a system. The system can include fewer or more components than those shown in the illustrations.

DETAILED DESCRIPTION

Certain specific illustrations of devices and systems that can be used to administer nuclear medication in an automated manner are described below. For example, the system can be loaded with nuclear medication in the form of a syringe contained within a shielded transportation container. The system can automatically gain access to the syringe and inject the into medication into a preloaded intravenous tube which is directed to the patient. The exact and number of components present may vary, and illustrative configurations are described below.

Certain configurations of the devices, systems and methods described herein can provide significant features including, for example, the ability to standardize flow rate and remove human hands from the choice of flow rate, the ability to standardize flow rate under medical direction to reduce infiltration and dose delivery error, the ability to remove hands from dose delivery to reduce radiation dose to staff, the ability to add distance from staff and patient to improve as low as reasonably achievable (ALARA) radiation exposure and lower exposure, the ability to remove heavy syringe shields from the hands of staff to reduce error and expense of syringe shield devices, and the ability to utilize unit dose in an automated machine to improve regulatory compliance and reduce/eliminate punctures on bulk vials.

In certain embodiments, the administration of nuclear medication being given to a patient is typically delivered through a system comprised of an intravenous (IV) bag hanging from an IV pole and a syringe, containing the medication, with IV tubing being routed to the patient. The duration of the process of administration can typically last many minutes, during which time the nuclear medication within the IV bag is emitting a significant amount of radioactivity into all areas of the local treatment theater. This radioactive emission poses a serious exposure risk to all attending medical staff. The devices and systems described herein can be used to deliver the medication to the patient without the medical staff ever having to directly handle or touch the IV bag or syringe being used to hold the nuclear medication.

In certain examples, nuclear medication administered using the devices and systems described herein can be delivered to the location of use within a syringe, typically sized from 3 mL to 10 mL in size. This syringe can be delivered within a cylindrically-shaped shielded transport container (sometimes referred to as a "pig") constructed primarily of lead. This transport container can include access covers, or caps, to allow installation, removal and access to the syringe located inside. The enclosure and covers of the transport container can be constructed from lead or other radiation attenuating materials as appropriate.

Figure 1A:
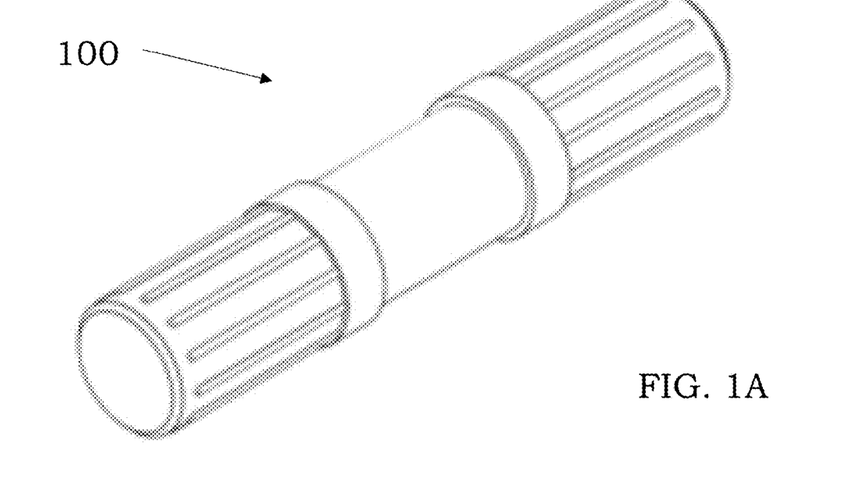
FIG. 1A is a perspective view of a shielded transport container with access covers attached, in accordance with certain configurations.
Figure 1B:
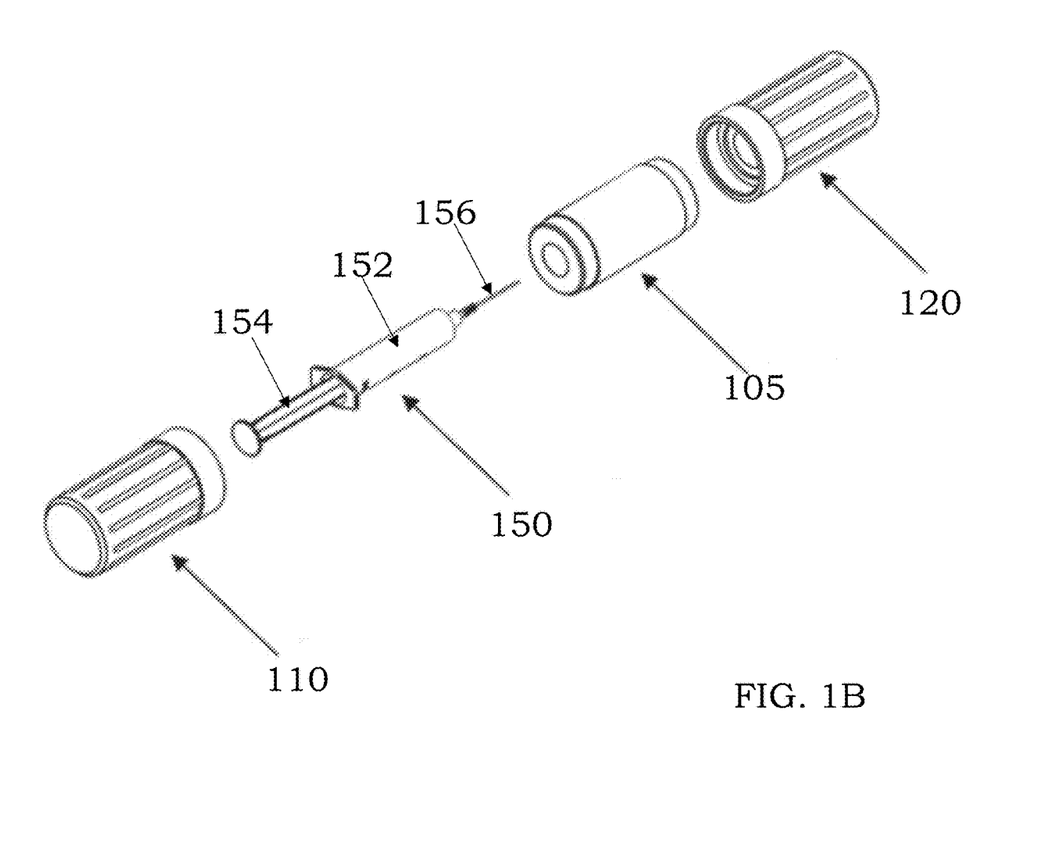
FIG. 1B is a perspective view of different components of a shielded transport container and a syringe, in accordance with some embodiments.

Referring to FIGS. 1A and 1B, an illustrative transport container 100 is shown that comprises end caps 110, 120 and a body 105. The end caps 110, 120 can couple to the body 105 in a reversible manner and desirably can be removed using an actuator, motor or other means in an automated manner. A syringe 1050 is shown for reference. The syringe 150 can fit into the body 105 by way of a friction fit to retain the barrel 152 the syringe 150 in the body 105. If desired, an opening 107 in the body can include high friction materials to assist in retaining the barrel 152 in the body 105. A plunger 154 and a needle 156 are exposed when the barrel 152 is inserted into the body 105. As noted below, during use of the syringe 150 positioned within the body 105, the plunger 154 can be depressed in an automated manner to introduce the nuclear medication within the barrel 152 into the needle 156 and to an injection port fluidically coupled to an intravenous line of a patient. This introduction may be performed in an automated manner in a shielded system to prevent exposure of any staff to radiation from the nuclear medication.

Figure 2A:
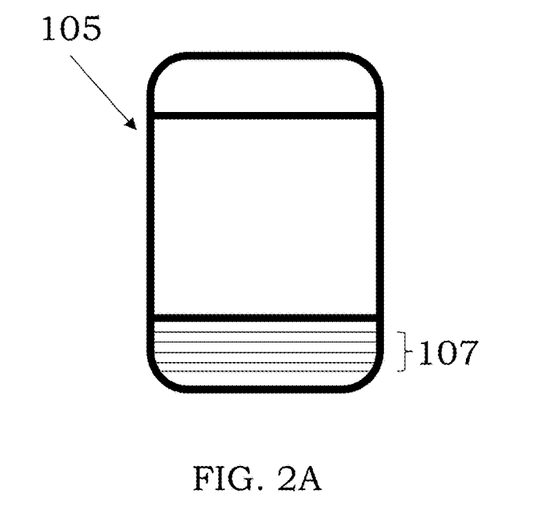
FIGS. 2A, 2B, and 2C show different configurations of a shielded transport container body, in accordance with certain embodiments.
Figure 2B:
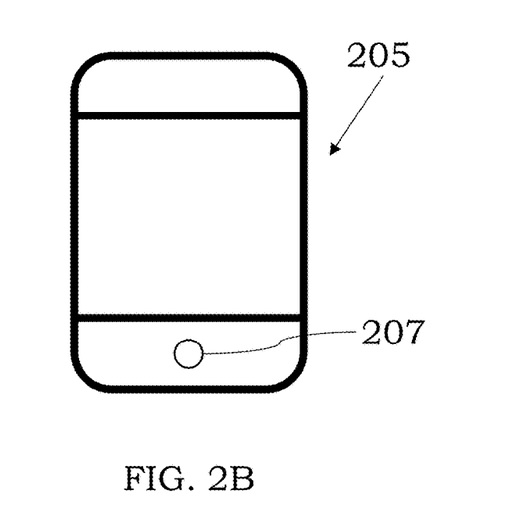
Figure 2C:
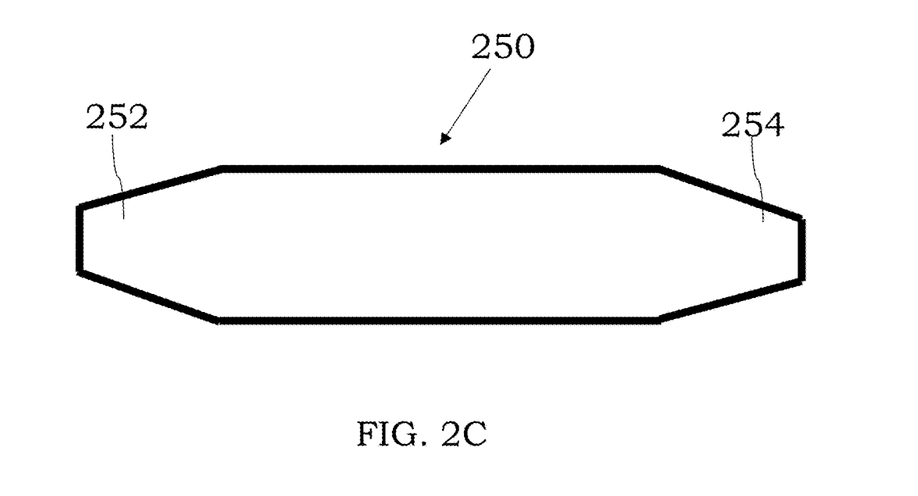

In certain embodiments, the body 105 can include threads 107 on one or both ends of the body as shown in FIG. 2A. Corresponding threads can be present on the access covers that can securely mate to the threads 107 to seal the syringe 150 and nuclear medication within a shielded container. As noted below, actuators can grasp access covers and rotate the access covers to unthread the access covers from the body to expose the plunger and needle. In certain embodiments, the body can be configured with features other than threads to secure the access covers to the body. Referring to FIG. 2B, a body 205 is shown that includes a hole or aperture 207 that can receive a spring-loaded button on an access cover. Depression of the spring-loaded button can permit insertion and secure retention of the access cover to the body 205. The button can then be depressed by an actuator to remove the access cover to the plunger and/or needle. In an alternative configuration (FIG. 2C), a body 250 may have tapered ends 252, 254 that can couple to the access covers by way of a friction fit. For example, the access covers can slide onto the ends 252, 254 until they are retained. An actuator can remove the actuators by sliding them off the ends 252, 254 to expose the plunger and needle. Other configurations to reversibly couple the access covers and the body are also possible.

In certain embodiments, the outer cross-section of the shielded transport container need not be circular as shown in FIGS. 1A and 1B. For example, the outer cross-section of the shielded transport container may be square, elliptical, triangular or take other shapes. Similarly, the inner cross-section could have shapes other than circular. Notwithstanding that many different shapes are possible for the inner cross-section, the body of the shielded transport container desirably holds the syringe in a secure manner during administration of the nuclear medication in the syringe.

Figure 3A:
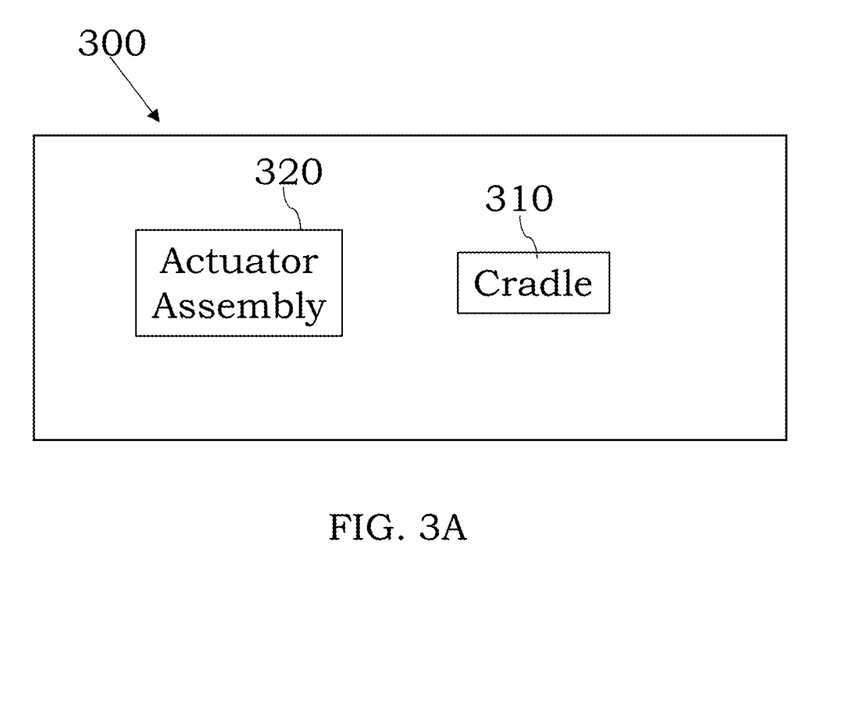
FIG. 3A is a block diagram of certain components in a system including a cradle and an actuator, in accordance with some embodiments.
Figure 3B:
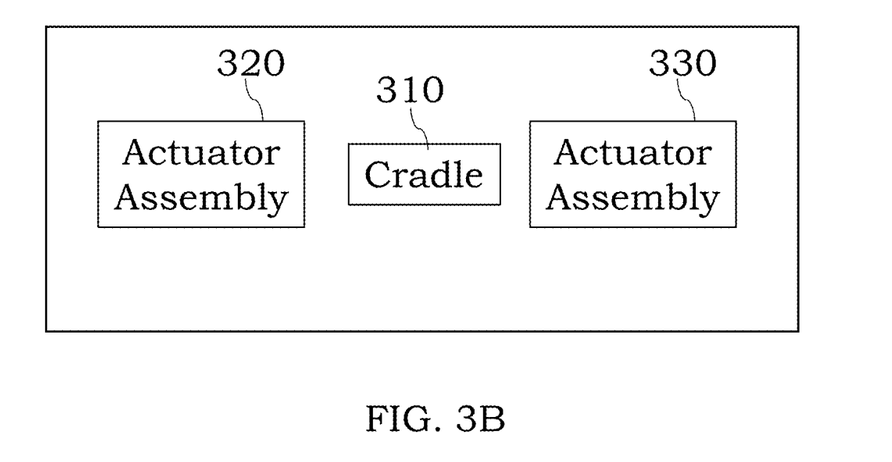
FIG. 3B is a block diagram of certain components in a system including a cradle and two actuators, in accordance with some embodiments.

In certain embodiments, the shielded transport container can be used with a system designed to receive the shielded container, remove the access caps and inject the nuclear medication into the intravenous line or a port connected thereto. A simplified block diagram of certain components are shown in FIG. 3A. The system 300 includes a cradle 310 configured to receive the shielded transport container (not shown). The system 300 can include at least one actuator assembly 320 that is configured to reversibly couple to an access cover or both access covers of the shielded transport container when placed into the cradle 300. For example, the actuator 320 may grasp or otherwise engage the access cover to rotate and unscrew the access cover(s) of the shielded transport container to expose the plunger or the needle or both. In instances where the access covers fit onto the body of the shielded transport container through a friction fit, the actuator 320 may be a linear actuator that can grasp the access cover and apply a force to remove it from the body. In other examples, the actuator 320 can be a rotary actuator that can grasp or contact the access cover and rotate it for removal from the body to expose the plunger or syringe. In some embodiments, two actuator assemblies can be present as shown in FIG. 3B, with a second actuator assembly 330 configured to contact a second access cover of the shielded transport container. In some instances, each of the actuators 320 and 330 is a linear actuator. In other embodiments, at least one of the actuators 320, 330 is a rotary actuator. In some instances, each of the actuators 320, 330 is a rotary actuator. In certain embodiments, the actuators described herein can include a motor, gears, pistons, etc. For example, the actuator can include one or more of a stepper motor, servomotor or other types of motors. The actuator(s) may be electrically powered, pneumatically powered or hydraulically powered as desired. The actuators can include pistons, arms, fingers, grasping surfaces or other features to contact the access covers.

Figure 4A:
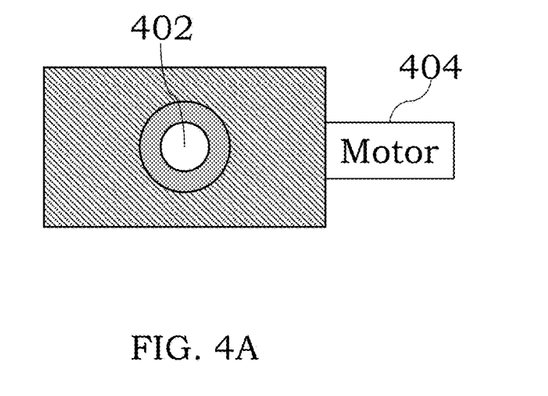
FIG. 4A is an illustration of a rotary actuator, in accordance with certain configurations.

In some embodiments where a rotary actuator is used to remove an access cover, the rotary actuator can include a cylindrical member that can engage the access cover through a friction fit. A simplified illustration is shown in FIG. 4A, where an actuator 400 includes a cylindrical member 402 that can slide or project to contact outer surfaces of an access cover. The cylindrical member 402 can be coupled to a motor 404 and optionally gears, differentials, joints, etc. to permit rotation of the cylindrical member 402. After contacting the access cover, the cylindrical member 402 may rotate, e.g., counterclockwise, to cause a corresponding rotation of the access cover. This rotation can release the access cover from the shielded transport container. The actuator 400 can then move away from the body of the shielded transport container, e.g., the actuator 402 can be positioned on a movable stage or gantry that can move the actuator 402 toward and/or away from the cradle containing the shielded transport container. Moving away of the actuator 402 and coupled access cover exposes the plunger or needle of the syringe (not shown). If desired, the actuator 402 can include an arm, fingers or other devices to assist in grasping of the access cover(s) of the shielded transport container to facilitate removal.

Figure 4B:
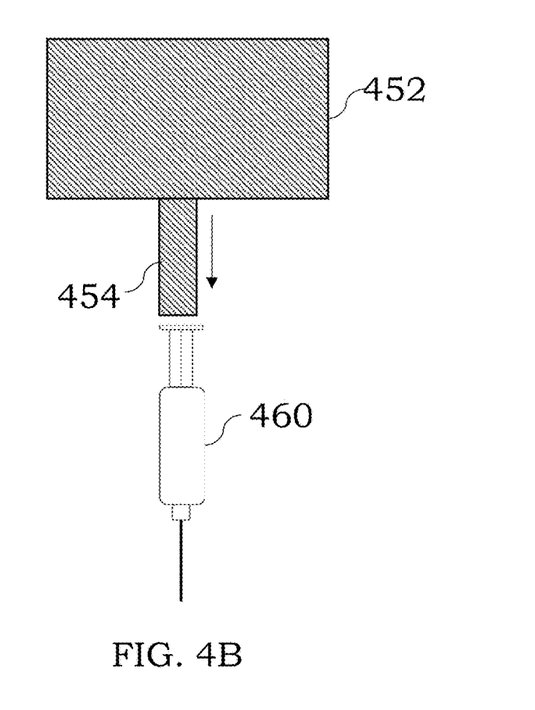
FIG. 4B is an illustration of a linear actuator and a syringe, in accordance with certain configurations.

In certain embodiments, one of the actuators present in the system may be a linear actuator that can depress the plunger of the syringe after the plunger is exposed. Referring to FIG. 4B, a linear actuator 452 with a piston 454 is shown. The piston 454 can move in the direction shown by the arrow to contact a plunger of the syringe 460. The piston 454 can be coupled to a motor to move the piston in a selected direction and at a selected speed. The speed, for example, can be selected based on a desired administration rate of the nuclear medication. The depression rate of the plunger by the piston 454 may be constant over a treatment period or may be variable over the treatment period. In some embodiments, total movement of the piston 454 can be used as an indicator that the plunger has been fully depressed and that treatment has ended.

In certain embodiments, the cradle present in the systems described herein is generally configured to receive and retain the shielded transport container. The cradle itself, if desired, may also provide some degree of radiation shielding. In some embodiments, the cradle can receive and retain the shielded transport container by way of a friction fit, clamps, spring-loaded arms or other devices that can securely retain a generally cylindrical body for at least some period. The force used to retain the shielded transport container is typically larger than any force used to depress a plunger of a syringe within the body of the shielded transport container. Desirably, depression of the plunger of a syringe held in a shielded transport container retained by a cradle does not move the syringe to any substantial degree.

Figure 5:
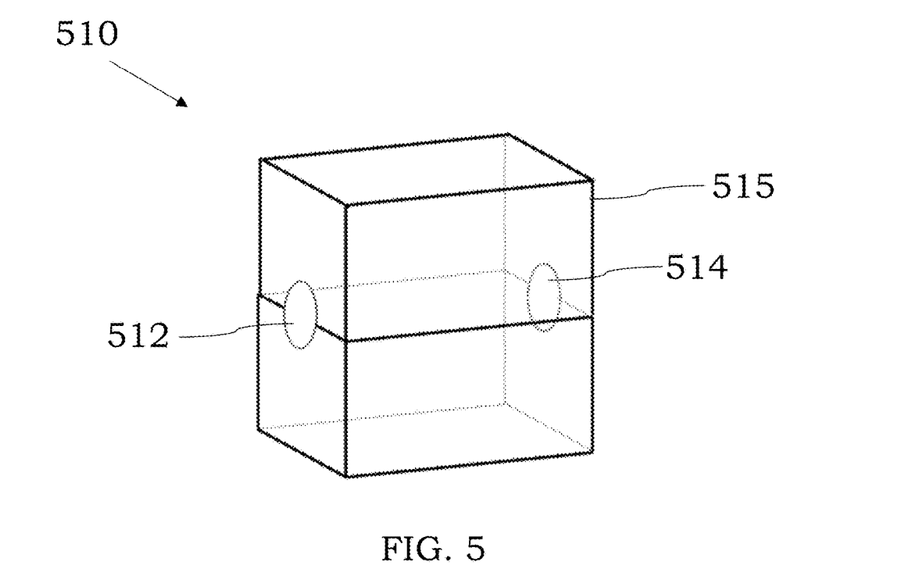
FIG. 5 is a block diagram of a system that can be used to inject a nuclear medication into a patient, in accordance with some embodiments.

In certain configurations, one illustration of a cradle is shown in FIG. 5. The cradle is generally configured as a box 510 comprising an opening, e.g., openings 512, 514, on each side of the box 510. The box 510 can include a lid 515 on a hinge (not shown) that permits exposure of an interior of the box 510 to permit placement of a shielded transport container within the box 510. Alternatively, the box 510 could include a bottom section and a top section that is separable from the box 510. Notwithstanding that the cradle can be configured in many different ways, opening of the box 510 permits placement of a shielded transport container inside of the box 510. The access covers of the shielded transport container can protrude through the openings 512, 514 on each side of the box 510 such that the actuators can contact and remove the access covers. In some embodiments, the box 510 may comprise one or more shielding materials to prevent or reduce the amount of radiation emitted. Illustrative shielding materials include, but are not limited to, one or more of lead, antimony, bismuth, tungsten and tin. Alternatively, the cradle could be produced from polymeric material such as plastics or other materials. In some instances, the position of the cradle can be fixed, whereas in other configurations, the cradle can move or be moveable to alter a position of the cradle during use. For example, the cradle may move after a needle is exposed to fluidically couple the exposed needle to an injection port connected to an intravenous line of the patient. Alternatively, the cradle may rotate by 180 degrees to permit a single rotary actuator to remove two access covers sequentially from the shielded transport container.

Figure 6A:
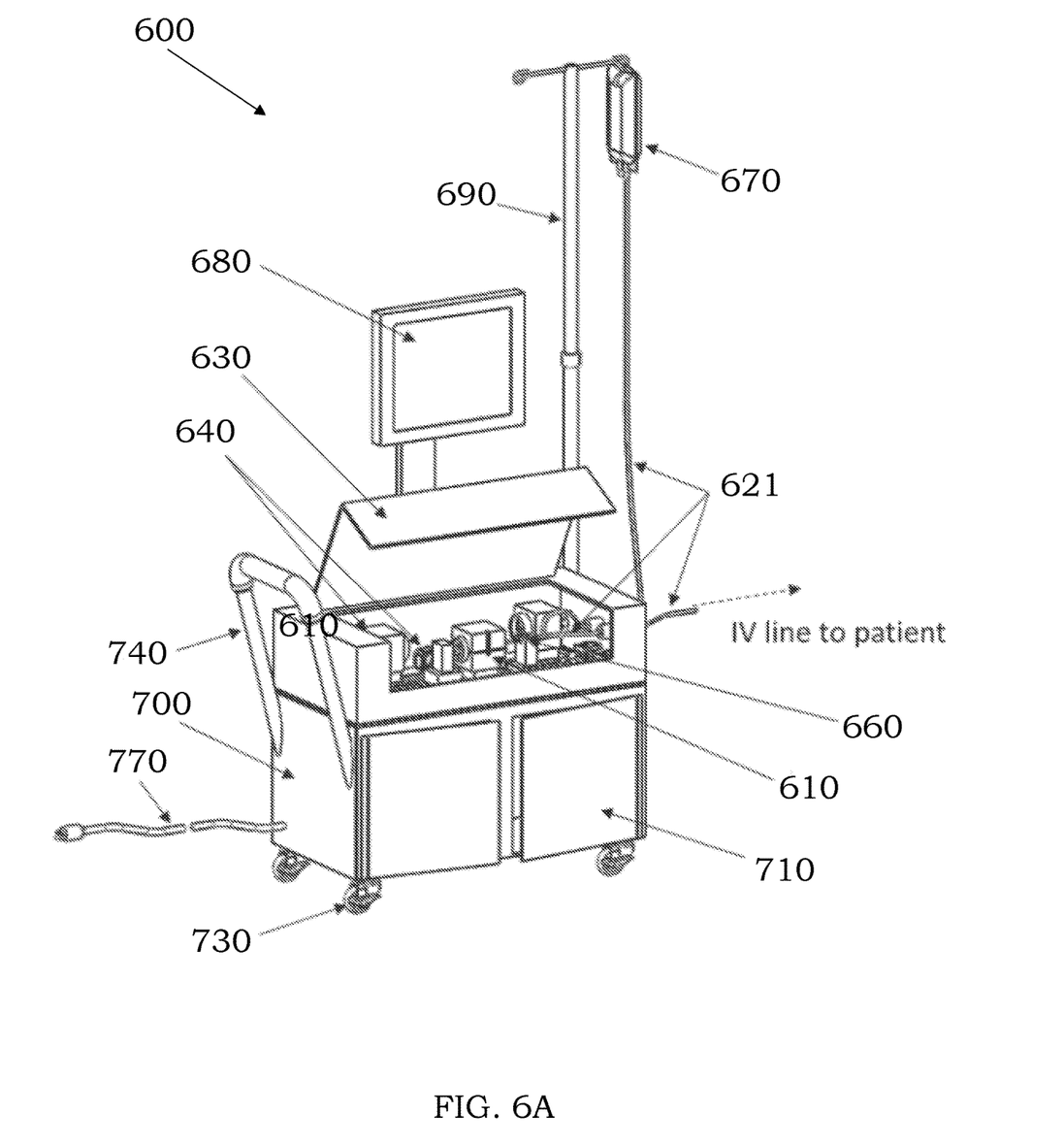
FIGS. 6A and 6B are illustrations of a system that can be used to administer a nuclear medication in an automated manner.
Figure 6B:
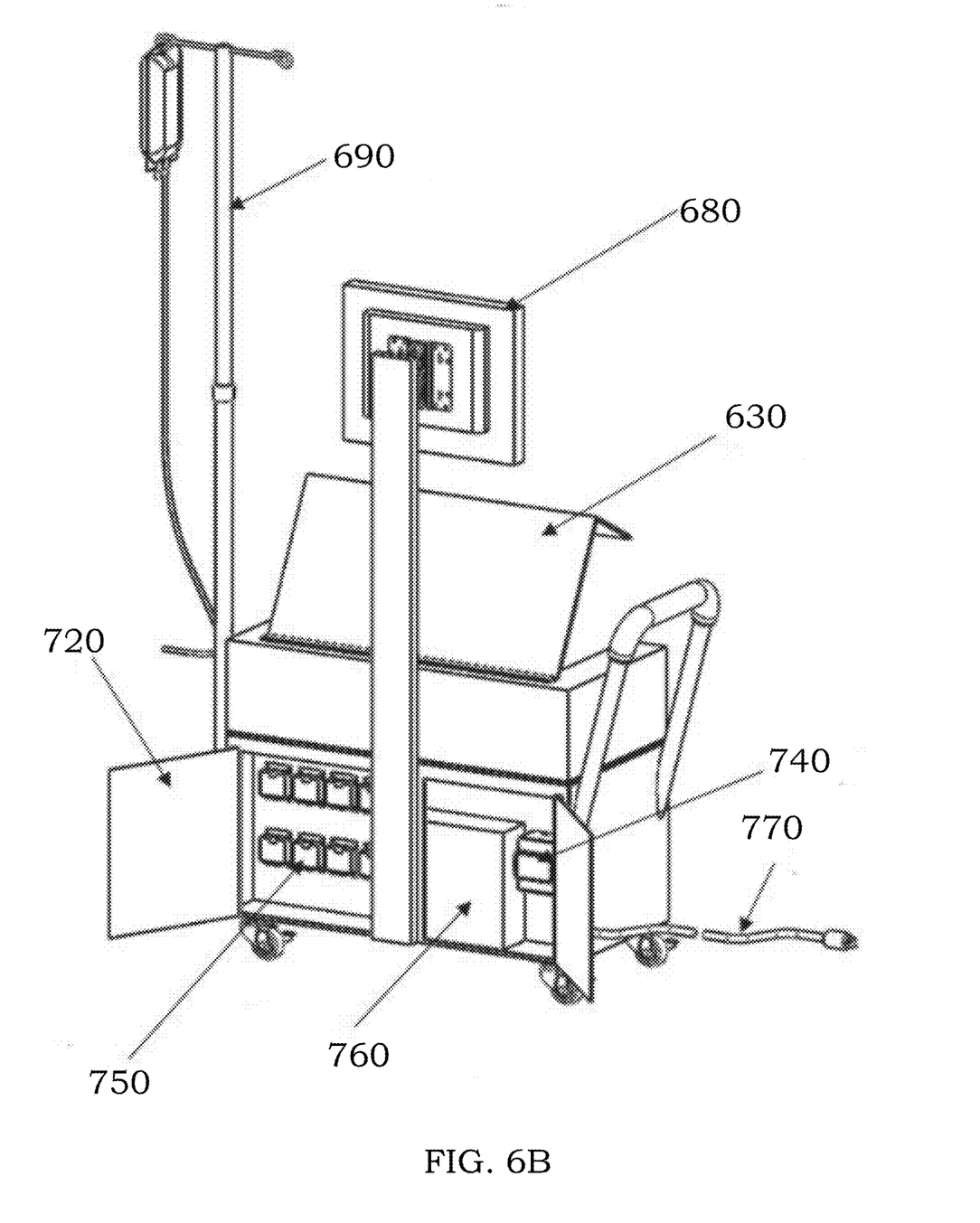

In certain embodiments, a system to deliver a nuclear medication in an automated manner can include other components. One illustration of a system is shown in FIGS. 6A and 6B. The system 600 is described below in reference to receipt of a cylindrically shaped shielded transport container, but the design of the cradle of the system may be altered to accept other shaped shielded transport containers. Upon insertion of the transport container into the system 600, the system 600 can automatically and robotically opens the inserted shielded transport container, gains access to the syringe in the inserted shielded transport container, connects the syringe to a preloaded IV tubing injection port 622, and injects the contents of the syringe into the IV tubing 621 that is directed to the patient. As noted herein, rotary and linear actuators within the system 600 serve to remove the access the covers from the shielded transport container, move the syringe to the desired position, and then actuate the plunger of the syringe to deliver the medication at the desired rate into the injection port 660. The system 600 is fully programmable for the rate of prescribed infusion. If desired, the infusion rate can be dependent on backpressure within the IV tubing using pressure sensors integrated into the device. The system 600 can also monitor the level of radioactivity of the medication as it is being administered using appropriate radiometric sensors in order to assure and verify the prescribed medication is being administered.

In use of the system, the shielded transport container is first placed into a cradle 610 within the system 600, and can be clamped in place or otherwise held securely by the cradle 610. IV tubing 621 and an IV injection port 660 is also loaded into the device. The lid 630 is then closed and locked. The system 600 can include safety measures to prevent operation of the system while the lid 630 is open. For example, the motor of the system can be disabled until the lid 630 is placed in a closed position. The lid 630 may also be locked prior to the system initiating treatment to prevent unwanted exposure of staff during the treatment process. These safety features reduce the likelihood that staff members will be exposed to radiation. If desired, the lid 630 can also include one or more shielding materials, e.g., lead, antimony, bismuth, tungsten and tin.

Once the lid 630 is closed, actuators in an actuator assembly 640 are then automatically moved into place which grip the removable access covers of the shielded transport container, and rotate and translate as necessary to remove the covers and expose the ends of the syringe located inside. The cradle 610 holding the body of the shielded transport container (and the syringe) is then automatically moved into a position that is aligned with an IV injection port 660 attached to the IV tubing 621. The IV injection port 660 is then translated into a position in which the needle of the syringe fully engages and penetrates the injection port 660. One final actuator, e.g., a linear actuator, can be configured to engage the plunger of the syringe and serves to force the medication from the syringe into the IV tubing. Injection rate of the medication is easily controlled by movement of the plunger actuator.

Once sufficient time has passed after the administration of the medication to the patient, or after a pre-selected time has passed, the lid 630 of the device may be safely unlocked (or may automatically unlock) and be opened and the syringe and IV tubing removed and discarded, and the elements of the shielded transport container may be removed for reuse. A touchscreen monitor 680 is shown and permits programming of infusion rate and for the display of levels of radioactivity. The system 600 can include a communication interface that has the seamless capability to digitally communicate with the medical facility information system to permanently and safely record all relevant data, e.g., in an electronic medical record of the patient. An IV pole 690 is shown to allow for the connection of an IV bag 670 to supplement the flow of the nuclear medication to the patient.

In certain configurations, the cradle and actuator can be present as a shielded automation subassembly that can be mounted to a cabinet 700. The rear-facing doors 720 of the cabinet provide access to a rear-facing compartment intended for the mounting of a control computer 740, house the servo motor drives 750 of the linear and rotary actuator assembly 640, and house the battery/power supply 760. The device is capable of operating from battery power or from wall power via the power cord 770. controlled with the motion of the plunger actuator. The front-facing doors 710 of the cabinet provides for storage of the consumable supplies, such as IV tubing sets. The entire system 600 can be mounted on casters 730 and also can include a handle 740 to allow for easy transport within the hospital environment. Alternatively, the system could instead be a tabletop system or have other form factors than what is shown in FIGS. 6A and 6B. The cabinet 700 can be produced, or include, shielding materials such as, for example, lead, antimony, bismuth, tungsten and tin. These materials may be present as a lining or within or on the various panels of the cabinet 700.

In some embodiments, the control computer 740 can include one or more processors. The processor of the devices and systems described herein can also generally control the system if desired. For example, the various components of the systems described herein may be controlled using one or more processors, which can be part of the overall or present as a separate system through an associated device, e.g., computer, laptop, mobile device, etc. For example, the processor can be used to determine the radiation levels, determine if treatment should continue, control the actuators, determine if the lid is closed, can write a treatment record to an electronic medical record, and otherwise control other parameters of the process and system. Such processes may be performed automatically by the processor without the need for user intervention or a user may enter parameters through a user interface. In certain configurations, the processor may be present in one or more computer systems and/or common hardware circuitry including, for example, a microprocessor and/or suitable software for operating the system, e.g., to measure the radiation, etc. The processor can be integral to the system or may be present on one or more accessory boards, printed circuit boards or computers electrically coupled to the components of the in-line system. The processor is typically electrically coupled to one or more memory units to receive data from the other components of the system and permit adjustment of the various system parameters as needed or desired. The processor may be part of a general-purpose computer such as those based on Unix, Intel PENTIUM-type processor, Intel Core™ processors, Intel Xeon™ processsors, AMD Ryzen™ processors, AMD Athlon™ processors, AMD FX™ processors, Motorola PowerPC, Sun UltraSPARC, Hewlett-Packard PA-RISC processors, Apple-designed processors including Apple A14 Bionic processor, A13 Bionic processor, A12 processor, Apple A11 processor and others or any other type of processor. One or more of any type computer system may be used according to various embodiments of the technology. Further, the system may be connected to a single computer or may be distributed among a plurality of computers attached by a communications network. If desired, different components of the in-line system may be controlled by a respective processor or computer that is separate from a processor or computer used to control other components of the in-line system. It should be appreciated that other functions, including network communication, can be performed and the technology is not limited to having any particular function or set of functions. Various aspects may be implemented as specialized software executing in a general-purpose computer system. The computer system may include a processor connected to one or more memory devices, such as a disk drive, memory, or other device for storing data. Memory is typically used for storing radiation measurements, treatment routines, electronic medical records and other values. Components of the computer system may be coupled by an interconnection device, which may include one or more buses (e.g., between components that are integrated within a same machine) and/or a network (e.g., between components that reside on separate discrete machines). The interconnection device provides for communications (e.g., signals, data, instructions) to be exchanged between components of the system. The computer system typically can receive and/or issue commands within a processing time, e.g., a few milliseconds, a few microseconds or less, to permit rapid control of the system. The processor typically is electrically coupled to a power source which can, for example, be a direct current source, an alternating current source, a battery, a solar cell, a fuel cell or other power sources or combinations of power sources. The power source can be shared by the other components of the system. The system may also include one or more input devices, for example, a keyboard, mouse, trackball, microphone, touch screen, manual switch (e.g., override switch) and one or more output devices, for example, a printing device, display screen, speaker. For example, the input devices can permit a user to enter parameters about the particular nuclear medication being used, display an electronic medical record or provide other input and/or output features. If desired, a user interface can be present on a mobile device, laptop, tablet, etc., that can communicate with the system and permit entry of parameters or other information into the system by way of the mobile device, laptop, tablet, etc. In addition, the system may contain one or more communication interfaces that connect the computer system to a communication network (in addition or as an alternative to the interconnection device). The system may also include suitable circuitry to convert signals received from the various electrical devices present in the systems. Such circuitry can be present on a printed circuit board or may be present on a separate board or device that is electrically coupled to the printed circuit board through a suitable interface, e.g., a serial ATA interface, ISA interface, PCI interface, a USB interface, a Fibre Channel interface, a Firewire interface, a M.2 connector interface, a PCIE interface, a mSATA interface or the like or through one or more wireless interfaces, e.g., Bluetooth, Wi-Fi, Near Field Communication or other wireless protocols and/or interfaces.

In certain embodiments, the storage system used in the systems described herein typically includes a computer readable and writeable nonvolatile recording medium in which codes of software can be stored that can be used by a program to be executed by the processor or information stored on or in the medium to be processed by the program. The recording medium may, for example, be a hard disk, solid state drive or flash memory. The program or instructions to be executed by the processor may be located locally or remotely and can be retrieved by the processor by way of an interconnection mechanism, a communication network or other means as desired. Typically, in operation, the processor causes data to be read from the nonvolatile recording medium into another memory that allows for faster access to the information by the processor than does the medium. This memory is typically a volatile, random access memory such as a dynamic random access memory (DRAM) or static memory (SRAM). It may be located in the storage system or in the memory system. The processor generally manipulates the data within the integrated circuit memory and then copies the data to the medium after processing is completed. A variety of mechanisms are known for managing data movement between the medium and the integrated circuit memory element and the technology is not limited thereto. The technology is also not limited to a particular memory system or storage system. In certain embodiments, the system may also include specially-programmed, special-purpose hardware, for example, an application-specific integrated circuit (ASIC), microprocessor units MPU) or a field programmable gate array (FPGA) or combinations thereof. Aspects of the technology may be implemented in software, hardware or firmware, or any combination thereof. Further, such methods, acts, systems, system elements and components thereof may be implemented as part of the systems described above or as an independent component. Although specific systems are described by way of example as one type of system upon which various aspects of the technology may be practiced, it should be appreciated that aspects are not limited to being implemented on the described system. Various aspects may be practiced on one or more systems having a different architecture or components. The system may comprise a general-purpose computer system that is programmable using a high-level computer programming language. The systems may be also implemented using specially programmed, special purpose hardware. In the systems, the processor is typically a commercially available processor such as the well-known microprocessors available from Intel, AMD, Apple and others. Many other processors are also commercially available. Such a processor usually executes an operating system which may be, for example, the Windows 7, Windows 8 or Windows 10 operating systems available from the Microsoft Corporation, MAC OS X, e.g., Snow Leopard, Lion, Mountain Lion, Mojave, High Sierra, El Capitan or other versions available from Apple, the Solaris operating system available from Sun Microsystems, or UNIX or Linux operating systems available from various sources. Many other operating systems may be used, and in certain embodiments a simple set of commands or instructions may function as the operating system.

In certain examples, the processor and operating system may together define a platform for which application programs in high-level programming languages may be written. It should be understood that the technology is not limited to a particular system platform, processor, operating system, or network. Also, it should be apparent to those skilled in the art, given the benefit of this disclosure, that the present technology is not limited to a specific programming language or computer system. Further, it should be appreciated that other appropriate programming languages and other appropriate systems could also be used. In certain examples, the hardware or software can be configured to implement cognitive architecture, neural networks or other suitable implementations. If desired, one or more portions of the computer system may be distributed across one or more computer systems coupled to a communications network. These computer systems also may be general-purpose computer systems. For example, various aspects may be distributed among one or more computer systems configured to provide a service (e.g., servers) to one or more client computers, or to perform an overall task as part of a distributed system. For example, various aspects may be performed on a client-server or multi-tier system that includes components distributed among one or more server systems that perform various functions according to various embodiments. These components may be executable, intermediate (e.g., IL) or interpreted (e.g., Java) code which communicate over a communication network (e.g., the Internet) using a communication protocol (e.g., TCP/IP). It should also be appreciated that the technology is not limited to executing on any particular system or group of systems. Also, it should be appreciated that the technology is not limited to any particular distributed architecture, network, or communication protocol.

In some instances, various embodiments may be programmed using an object-oriented programming language, such as, for example, SQL, SmallTalk, Basic, Java, Javascript, PHP, C++, Ada, Python, iOS/Swift, Ruby on Rails or C#(C-Sharp). Other object-oriented programming languages may also be used. Alternatively, functional, scripting, and/or logical programming languages may be used. Various configurations may be implemented in a non-programmed environment (e.g., documents created in HTML, XML or other format that, when viewed in a window of a browser program, render aspects of a graphical-user interface (GUI) or perform other functions). Certain configurations may be implemented as programmed or non-programmed elements, or any combination thereof. In some instances, the systems may comprise a remote interface such as those present on a mobile device, tablet, laptop computer or other portable devices which can communicate through a wired or wireless interface and permit treatment using the nuclear medication as desired.

In certain examples, the processor may also comprise or have access to a database of information about nuclear medications, radiation levels, treatment times, and other parameters used to treat a patient with a nuclear medicine. For example, specific treatment doses for a particular nuclear medication can be retrieved from the database and used by the system. The instructions stored in the memory can execute a software module or control routine for the system, which in effect can provide a controllable model of the system. The processor can use information accessed from the database together with one or software modules executed in the processor to determine control parameters or values for different components of the systems, e.g., different treatment times, different doses, different plunger depression rates, etc. Using input interfaces to receive control instructions and output interfaces linked to different system components in the system, the processor can perform active control over the system.

In certain configurations, the exact nuclear medication used with the devices, systems and methods described herein may vary. For example, lutetium-177-DOTATATE, lutetium-177-DOTATAC, yttrium-90-DOTATATE, or yttrium-90-DOTATAC can be used to treat neuroendocrine tumors. Strontium-189 chloride, samarium-153, radium-223 and radium-223 dichloride can be used to treat prostate cancer. Yttrium-90 ibritumomab tiuxetan and iodine-131 tositumomab can be used to treat indolent B-cell lymphoma. Yttrium-90 and iodine-131 can be used in tandem with monoclonal antibodies to treat non-Hodgkin's lymphoma. Samarium-153-EDTMP and strontium-89-chloride can be used for palliation of bone metastases. In other instances, a radionuclide material may comprise one or more of bromine-77, indium-111, iodine-123, and iodine-125, lutetium-177, holmium-166, rhenium-186, rhenium-188, copper-67, promethium-149, gold-199, technetium-99m, strontium-89, radium-223, gallium-68, thorium-227, actinium-225 and rhodium-105. Some of these radioisotopes can be used in imaging applications, whereas other radioisotopes, e.g., beta and alpha emitters, are typically used in targeted radionuclide therapy materials. The binding moiety used with the radionuclide may vary and can be based on heme rings, peptides, lipids or other groups that can bind specifically to a receptor on a cell. If desired, the nuclear medicine material can be packaged in a kit optionally inside the "pig" or other radiation shielding containers.

Figure 7A:
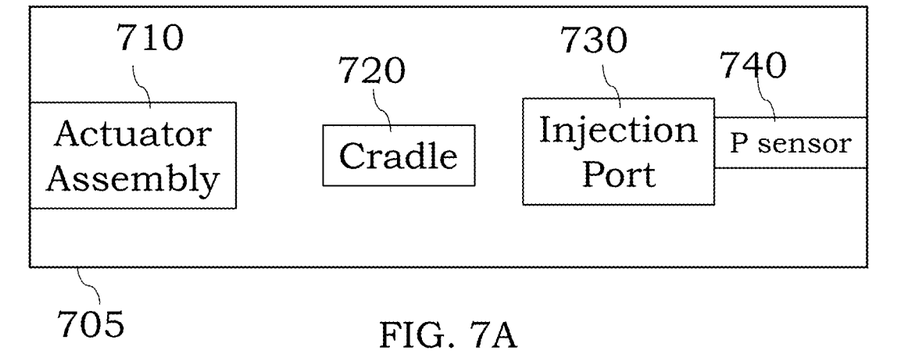
FIGS. 7A, 7B and 7C are illustrations of systems that can include one or more sensors, in accordance with certain configurations.
Figure 7B:
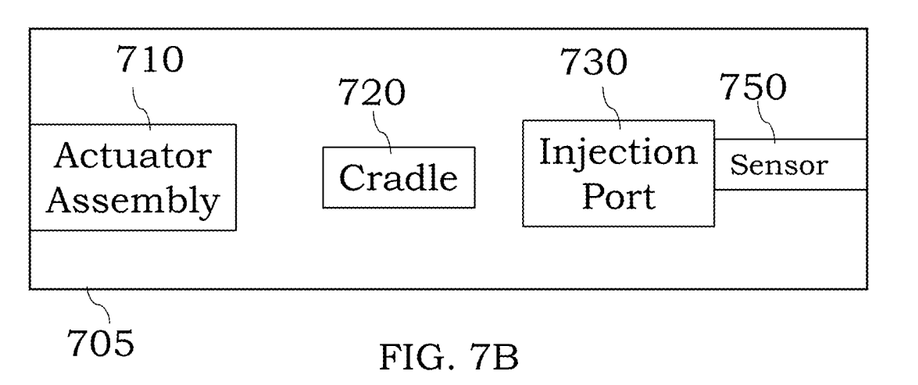
Figure 7C:
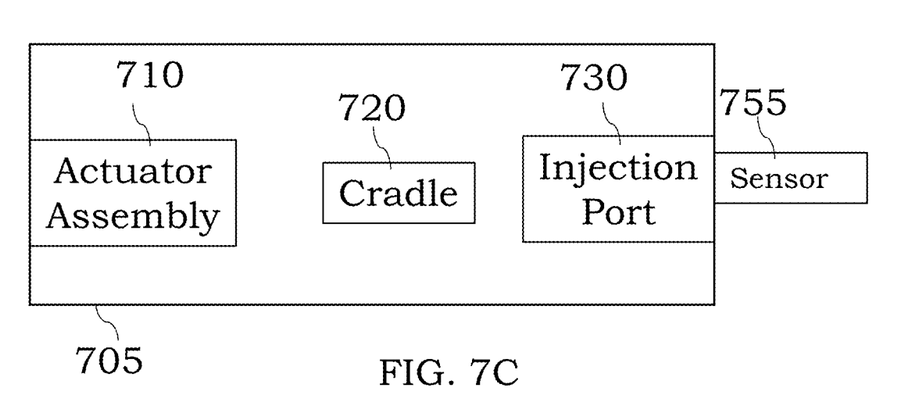

In certain embodiments, the systems and devices described herein can be used to inject a nuclear medication from a syringe into an intravenous fluid line of the patient in an automated manner after positioning the syringe into a system that shields an external user from radiation emitted by the nuclear medication. For example, the syringe can be positioned within a shielded transport container received by the system. Access covers of the shielded transport container can be removed automatically by the system, e.g., by the actuators, prior to injecting the nuclear medication from the syringe into the intravenous fluid line. For example, a first actuator can be configured to rotate an access cover off of each end of the shielded transport container to expose the needle and the plunger. The system can include a process that is configured to automatically actuate the first actuator after closing the lid. If desired, the system can include other components and devices as shown in FIG. 7A. For example, the system can include an actuator assembly 710, a cradle 720, an injection port 730 and a pressure sensor 740 within a housing 705. The pressure sensor 740 can be used to measure pressure in the intravenous fluid line during infusion of the nuclear medication to the patient. While not shown, the pressure sensor 740 could be positioned external to the housing 705 if desired. In some embodiments, the infusion rate can be controlled by controlling movement of a second actuator. The rate of movement of the second actuator corresponds to the rate of movement of the plunger of the syringe. In certain configurations, the system can include one or more radiometric probes or sensors, e.g., a Geiger counter, scintillation counter, etc., that can measure radiation, e.g., counts per second or counts per hour, of the nuclear medication being delivered to the patient. The sensor 750 can be internal to the housing (FIG. 7B) or external to the housing (FIG. 7C). For example, the sensor may be part of a device designed to hold a radiation probe as described in U.S. Application No. 62/976,285 filed on Feb. 13, 2020, the entire disclosure of which is hereby incorporated herein by reference.

In certain embodiments, the shielded transport containers may be present in a kit that includes the container and syringe with a nuclear medication. Alternatively, the kit may include the nuclear medication in another shielded container along with the shielded transport container. A syringe may or may not be present in the kit. Written or electronic instructions may be present in the kit to guide delivery of the nuclear medication to the patient for treatment.

When introducing elements of the examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

Although certain aspects, configurations, examples and embodiments have been described above, it will be recognized by the person of ordinary skill in the art, given the benefit of this disclosure, that additions, substitutions, modifications, and alterations of the disclosed illustrative aspects, configurations, examples and embodiments are possible.

What is claimed is:

1. A system for delivering a nuclear medication to a patient, the system comprising:
   a cradle configured to receive a shielded transport container, wherein the shielded transport container is constructed and arranged to receive a syringe with the nuclear medication;
   a lid configured to permit placement of the shielded transport container into the cradle in an open position and block access to the cradle in a closed position, wherein the lid is configured to shield an external user from radiation emitted from the nuclear medication in the syringe when the lid is in the closed position;
   a first actuator configured to contact and remove access covers of the shielded transport container to expose a needle end of the syringe and to expose a plunger of the syringe, wherein the first actuator is further configured to position the exposed needle end of the syringe to align the needle end of the syringe with an intravenous injection port fluidically coupled to an intravenous line connected to the patient;
   a second actuator configured to engage and depress the exposed plunger of the positioned syringe to inject the nuclear medication into the intravenous injection port; and
   a processor configured to control the first actuator and the second actuator.

2. The system of claim 1, wherein the second actuator is configured to inject the nuclear medication into the intravenous injection port incrementally over an infusion period.

3. The system of claim 1, wherein the first actuator is configured as a rotary actuator.

4. The system of claim 1, wherein the second actuator is configured as a linear actuator.

5. The system of claim 1, wherein each of the first actuator and the second actuator comprises a motor.

6. The system of claim 1, further comprising a pressure sensor, wherein the pressure sensor is configured to measure pressure in the intravenous line during infusion of the nuclear medication to the patient.

7. The system of claim 1, further comprising a lock configured to lock the lid in the closed position when the lid is closed after the shielded transport container is placed in the cradle.

8. The system of claim 7, wherein the processor is configured to automatically actuate the first actuator after closing the lid.

9. The system of claim 8, wherein the first actuator is configured to rotate an access cover off of each end of the shielded transport container to expose the needle and the plunger.

10. The system of claim 1, further comprising a display configured to permit entry of treatment parameters into the system.

11. A method of administering a nuclear medication to a patient, the method comprising injecting a nuclear medication from a syringe into an intravenous line of the patient in an automated manner after positioning the syringe into a system that shields an external user from radiation emitted by the nuclear medication, wherein the syringe is positioned within a shielded transport container received by the system, and wherein access covers of the shielded transport container are removed automatically by the system prior to injecting the nuclear medication from the syringe into the intravenous line.

12. The method of claim 11, wherein the system comprises:
- a cradle configured to receive a shielded transport container, wherein the shielded transport container is constructed and arranged to receive the syringe with the nuclear medication;
- a lid configured to permit placement of the shielded transport container into the cradle in an open position and block access to the cradle in a closed position, wherein the lid is configured to shield the external user from radiation emitted from the nuclear medication in the syringe when the lid is in the closed position;
- a first actuator configured to contact and remove access covers of the shielded transport container to expose a needle end of the syringe and to expose a plunger of the syringe, wherein the first actuator is further configured to position the exposed needle end of the syringe to align the needle end of the syringe with an intravenous injection port fluidically coupled to an intravenous fluid line connected to the patient;
- a second actuator configured to engage and depress the exposed plunger of the positioned syringe to inject the nuclear medication into the intravenous injection port; and
- a processor configured to control the first actuator and the second actuator.

13. The method of claim 11, wherein the first actuator is configured to rotate an access cover off of each end of the shielded transport container to expose the needle and the plunger.

14. The method of claim 11, wherein the processor is configured to automatically actuate the first actuator after closing the lid.

15. The method of claim 11, further comprising measuring pressure in the intravenous line during infusion of the nuclear medication to the patient.

16. The method of claim 11, further comprising controlling the second actuator to control the infusion rate of the nuclear medication.

17. The method of claim 11, further comprising measuring the radioactivity levels of the medication during infusion of the medication.

18. The method of claim 11, wherein the radioactivity levels are measured using a radiometric sensor.

19. The method of claim 11, wherein the radiometric sensor is positioned within the system.

20. The method of claim 11, wherein the radiometric sensor is positioned external to the system.

* * * * *